United States Patent [19]

Cox

[11] Patent Number: 4,979,505

[45] Date of Patent: Dec. 25, 1990

[54] TRACHEAL TUBE

[76] Inventor: Everard F. Cox, 4510 Mt. Carmel Rd., Hampstead, Md. 21074

[21] Appl. No.: 362,242

[22] Filed: Jun. 6, 1989

[51] Int. Cl.$^5$ .......................................... A61M 16/04
[52] U.S. Cl. ........................... 128/207.15; 128/207.14
[58] Field of Search ..................... 128/207.14, 207.15, 128/911

[56] References Cited

U.S. PATENT DOCUMENTS

| | | | |
|---|---|---|---|
| 2,923,299 | 2/1960 | Blackwood | 128/207.17 |
| 3,087,493 | 4/1963 | Schossow | 128/207.15 |
| 3,348,542 | 10/1967 | Jackson | 128/207.15 |
| 3,610,247 | 10/1971 | Jackson | 128/207.15 |
| 3,616,799 | 11/1971 | Sparks | 128/207.15 |
| 3,709,227 | 1/1973 | Hayward | 128/207.15 |
| 3,760,811 | 9/1973 | Andrew | 128/207.17 |
| 3,799,173 | 3/1974 | Kamen | 128/207.15 |
| 3,884,242 | 5/1975 | Bazell et al. | 128/207.15 |
| 3,890,976 | 6/1975 | Bazell et al. | 128/207.15 |
| 3,927,670 | 12/1975 | Turney | 128/719 |
| 3,931,822 | 1/1976 | Marici | 128/207.15 |
| 4,046,139 | 9/1977 | Horn | 128/207.15 |
| 4,064,882 | 12/1977 | Johnson | 128/207.15 |
| 4,134,407 | 1/1979 | Elam | 128/207.15 |
| 4,278,081 | 7/1981 | Jones | 128/207.15 |
| 4,329,993 | 5/1982 | Lieber | 604/98 |
| 4,340,046 | 7/1982 | Cox | 128/207.15 |
| 4,351,330 | 9/1982 | Scarberry | 128/207.15 |
| 4,362,166 | 12/1982 | Furler | 128/670 |
| 4,471,776 | 9/1984 | Cox | 128/207.15 |
| 4,502,482 | 3/1985 | DeLiccia et al. | 128/207.15 |
| 4,509,514 | 4/1985 | Brain | 128/207.15 |
| 4,584,998 | 4/1986 | McGrail | 128/207.15 |
| 4,850,348 | 7/1989 | Pell et al. | 128/207.15 |
| 4,872,483 | 10/1989 | Shah | 128/207.15 |

FOREIGN PATENT DOCUMENTS

| | | | |
|---|---|---|---|
| 0995542 | 8/1976 | Canada | 128/207.15 |
| 7513957 | 11/1975 | Denmark . | |
| 0010880 | 5/1980 | European Pat. Off. | 128/207.15 |
| 1594260 | 7/1970 | France . | |
| 6615648 | 5/1968 | Netherlands | 128/207.14 |
| 0589988 | 2/1978 | U.S.S.R. | 128/207.15 |
| 933307 | 1/1960 | United Kingdom . | |

OTHER PUBLICATIONS

"Tracheotomy and New Tracheal Tube", pp. 260–266, from *Surgery*, Feb., 1951, V29, #2.
Anaestheiologi und Intensivmedizin, Band 116, Acute Care.
The Pressblowing Option For Tough-to-blow-Parts.

*Primary Examiner*—Edgar S. Burr
*Assistant Examiner*—Kimberly L. Asher
*Attorney, Agent, or Firm*—Fishman, Dionne & Cantor

[57] ABSTRACT

An improved tracheal tube cuff for protection of the lungs against aspiration injury and for improved continuous oxygen administration is presented. The low pressure inflatable cuff of this invention attaches to the endotracheal end of a tube and can be placed within the trachea either transorally or through a tracheostomy. The cuff is approximately a pair of inverted paraboloids precisely located on the tube so that upon inflation or expansion under low pressure, the tube will open against the tracheal wall forming a proximal seal against aspirated substances and will open distally beyond the end of the tube to create a seal to gaseous substances under varying pressures such as, but not exclusively, oxygen.

27 Claims, 3 Drawing Sheets

TRACHEAL TUBE

BACKGROUND OF THE INVENTION

This invention relates to medical and surgical devices and in particular to medical and surgical devices used in conjunction with patient respiration problems. More specifically, this invention relates to a means for providing an airway for patients requiring mechanical assistance in breathing, and/or for conduction of anesthetic gas when a tube is placed in the trachea through the mouth, nose or during a tracheostomy.

In any situation where ventilatory support to control respiration is necessary, the use of cuffed preformed tracheal tubes, whether by oral—translaryngeal insertion or by placement through a tracheostomy, has become the standard of medical practice. Additionally, by means of the inflatable cuff placed distally on the tube and expanded with sufficient pressure against the tracheal wall to form a seal, the tracheobronchial tubes are protected from aspiration of gastric contents or other foreign matter. These devices are the essential means of controlling the exchange of blood gases by establishing a closed system whereby the gas pressure in the airway distal to the inflated cuff can be maintained at the desired level. These essential functions of cuffed preformed tracheal tubes are used during the delivery of anesthetic gases or oxygen in critical intensive care situations. This closed system of pulmonary ventilation is possibly the most important advance in modern anesthesia and in the care of the critically ill or trauma victim. Regardless of advances the future may bring in these areas, control of respiration will always be necessary and the use of the tracheal tubes as a conduit between the lungs and the extracorporeal support system will always be required.

Presently used tracheal tubes have several known design and functional deficiencies which create significant complications in their use. The more severe of these problems are related to the inflatable cuff and are directly proportional to: (1) the pressure within the cuff necessary to occlude the trachea to maintain respiration and (2) the duration of tracheal intubation. As cuff pressure exceeds the capillary pressure of the tracheal tissues, normally 25 mm of mercury, tissue anoxia occurs and varying degrees of tracheal injury result. The injuries range from mild erosion of the mucosa, to destruction of the tracheal cartilage rings, to segmental tracheomalacia with dilatation of the trachea. More dramatic is full thickness erosion, with perforation of the inominate artery anteriorly or posteriorly into the esophagus; either of these events being associated with a high rate of mortality. Late complications of tracheal stenosis, from mild to incapacitating obstruction are noted in the majority of patients requiring long term ventilatory support.

An attempt at solving the above-mentioned Problems is disclosed in my prior U.S. Pat. Nos. 4,340,046 and 4,471,776, both of which are fully incorporated herein by reference. These prior patents describe an improved tracheostomy tube having four distinctive features including a precision cuff fitted to each trachea, a flexible tube that will conform to any depth of the trachea within the neck, a self-locking clip that adjusts the tube securely to an neck regardless of the depth of the trachea, and a malleable but rigid obturator for ease of insertion.

The precision cuff of my prior patents is fitted to each trachea. The cuff of tracheal tubes of the prior art are not provided with this feature. Most tracheal tubes that are in use now and in the prior art have a soft cuff that, when inflated, assumes a fusiform shape presenting a narrow surface in contact with the trachea mucosa. Any prolonged pressure above twenty-five torr increases the risk of tracheal necrosis. In my prior patents, the improved precision cuff comprises a substantially convoluted or fluted cuff with constricting bands to limit distention to the specific size of each trachea.

The advantage of the precision convoluted-like or fluted cuff of my prior patents is to equalize the pressure over a longer segment of the mucosa by the use of the constricting bands limiting the size in the cuff constrictions. This also insures uniform diameter and controlled expansion.

The convoluted-like or fluted cuff and the manner of assuring the precise size in relation to the patient's trachea, effects a more complete seal at a lower pressure on the tracheal mucosa. Each convolution-like roll or flute creates a seal and the plurality of seals increases the total sealing effectiveness, thus avoiding the problem of the fusiform configuration which is inherent in the single chamber cuff.

While well suited for its intended purposes, the fluted cuff of my prior patents suffers from certain drawbacks and deficiencies and a need exists for an improved tracheal tube cuff.

SUMMARY OF THE INVENTION

The above-discussed and other problems and deficiencies of the prior art are overcome or alleviated by the present invention. In accordance with the present invention, a novel low pressure inflatable cuff is provided to the distal end of a tracheal tube. This cuff is approximately paraboloid shaped resembling an open tulip and is precisely located along the tracheal tube so that upon inflation, the cuff will extend beyond the distal end of the tube. In a preferred embodiment, the cuff of the present invention includes a first and a second paraboloid portion, the second paraboloid portion being inverted relative to the first paraboloid portion to approximate an hour glass configuration.

The present invention is designed to ameliorate the complications of the constant pressure of the inflatable cuff of the prior art and decrease injury associated with prolonged intubation. The low presssure cuff of this invention extends beyond the distal end of the tube to which it is attached and compensates for variable airway pressure. When in place within the lumen of the trachea, the cuff is opened with only enough pressure to bring it gently against the mucosa of the tracheal wall. As airway pressure fluctuates with ventilatory requirements of the lungs, this pressure is transmitted to the inflated cushion of the open cuff increasing the seal between the cuff and the tracheal wall. The higher the pressure within the tracheobronchial system, the tighter the seal, with maximum pressure occurring at the end of the inspiratory phase of respiration. At the conclusion of expiration, the pressure against the mucosa reverts to 0 mm of mercury or the pressure necessary to bring it to the wall to form the initial seal. Thus, there is intermittent compression of the capillary blood flow only during the inspiratory phase of respiration avoiding tissue necrosis associated with issue anoxia that accompanies the prolonged use of high cuff pressure necessary during some pathological states of the lungs.

Since the cuff distal to the end of the tube is designed specifically for respiratory control and is maintained expanded against the tracheal wall with minimal pressure, it is necessary to protect the pulmonary tree against aspiration of gastric contents, blood, and other secretions. This is accomplished in the preferred embodiment of this invention by placing a second paraboloid shaped cuff which is similar to the cuff on the distal end of the tube except that it is placed as an inverted paraboloid with the open end toward the larynx. This second paraboloid is also expanded with minimal pressure against the tracheal wall. Should aspiration occur, the fluids or particulate matter are effectively trapped in the opened reservoir created around the tube.

The above-discussed and other features and advantages of the present invention will be appreciated and understood by those skilled in the art from the following detailed description and drawings.

BRIEF DESCRIPTION OF THE DRAWINGS

Referring now to the drawings, wherein like elements are numbered alike in the several FIGURES.

DESCRIPTION OF THE PREFERRED EMBODIMENT

Figure 1:
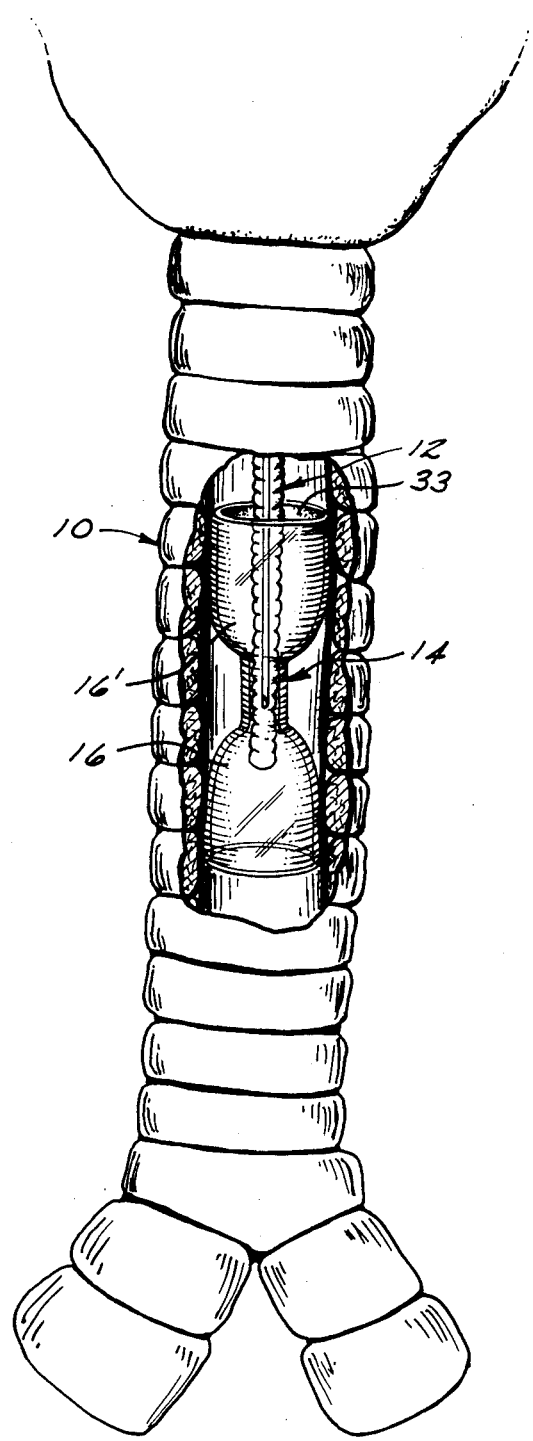
FIG. 1 is a front elevation view of a trachea depicting a tracheal tube having a novel cuff in accordance with the present invention inserted therein.

Referring first to FIG. 1, a human trachea is shown generally at 10 with a portion cut away depicting a tracheal tube 12 having been inserted therein in a known manner. In accordance with the present invention, a new and improved cuff means is shown generally at 14 being attached to the distal end of tracheal tube 12. It will be appreciated that cuff means 14 depicted in FIG. 1 is a preferred embodiment of the present invention more thoroughly explained with reference to FIGS. 4 and 5 below. A simplified, less preferred embodiment of this invention is depicted in FIGS. 2 and 3.

It will also be appreciated that the novel cuff means of the present invention may be utilized in conjunction with any known tracheal tube and should not be limited in any way to the particular tracheal tube shown in the FIGURES. Thus, only a portion of a tracheal tube is disclosed herein with the understanding that the present invention is applicable to any desired configuration or type of endotracheal tube in present use. Similarly, other known features associated with tracheostomy tubes such as a tube retainer or clip, obturator and like elements have not been shown in the drawings, but are well known to those skilled in the art; and also are disclosed in my earlier patents U.S. Pat. Nos. 4,340,046 and 4,471,776.

Figure 3:
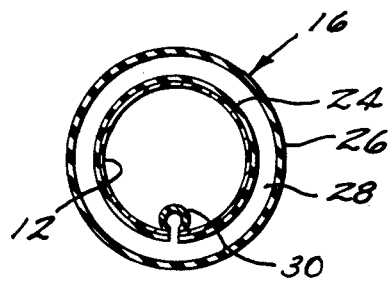
FIG. 3 is a cross sectional elevation view along the line 3—3 of FIG. 2.
Figure 2:
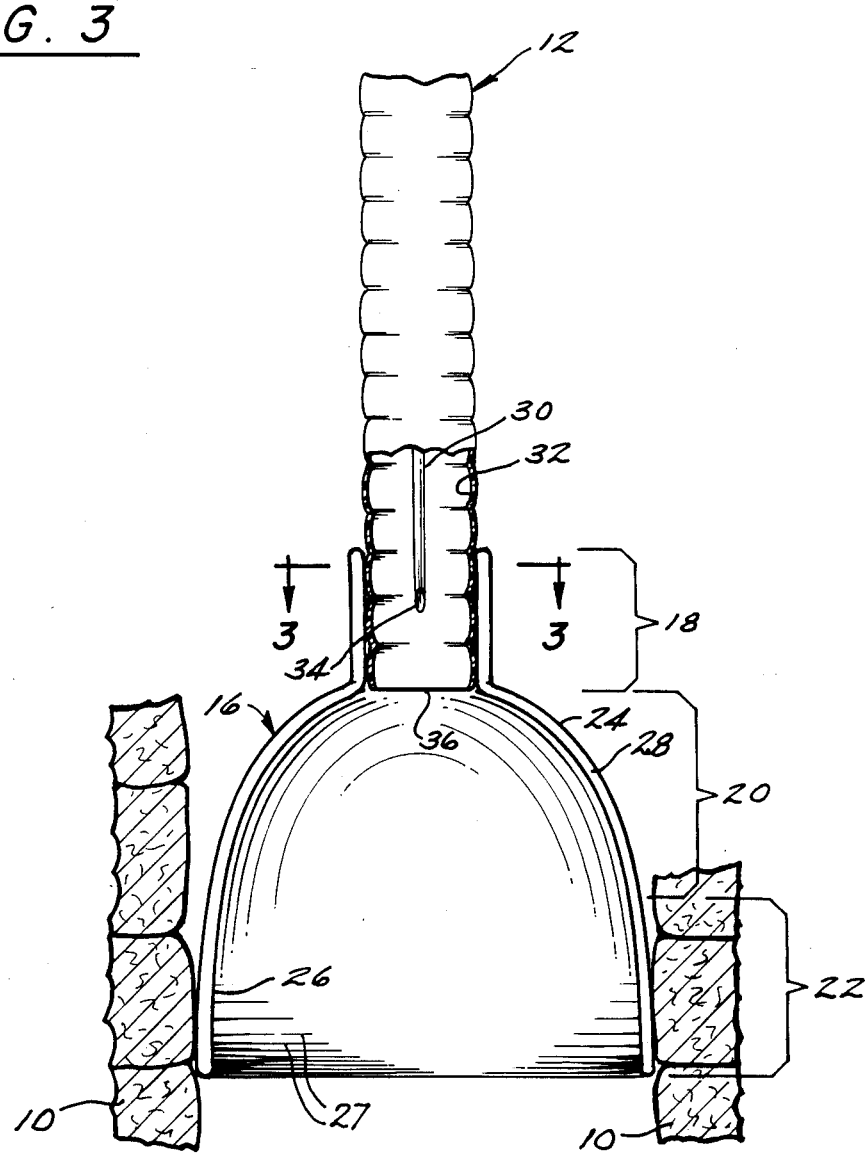
FIG. 2 is an enlarged view partly in cross section of a first embodiment of a cuff in accordance with the present invention.

Referring jointly now to FIGS. 2-3, a novel cuff means for use with a tracheal tube in accordance with a first embodiment of the present invention is shown generally at 16. "Cuff" 16 has an overall paraboloid shape analogous to that of an inverted tulip. More particularly, cuff 16 includes a neck portion 18 having a substantially constant diameter, a diverging portion 20 and a cylindrical skirt section 22. Cuff 16 includes an outer wall 24 and an inner wall 26 which define therebetween a central enclosed compartment or cavity 28. Cuff 16 is comprised of any suitable elastomeric material which will permit cavity 28 of cuff 16 to be inflated with a compressible fluid at low pressures (e.g. about 5-10 mm of mercury) to attain the tulip shape of FIG. 2. Accordingly, cuff 16 may be comprised of a polyvinyl chloride, polyurethane, or similar material.

Preferably, cavity 28 is broken up into a plurality of interconnected annular passageways. This is accomplished by bonding walls 24 and 26 at selected intervals identified by the lines 27 to produce a plurality of subchambers. These subchambers act to restrain the centripetal expansion of the cuff.

Still referring to FIGS. 2 and 3, fluid (e.g. air) is delivered to cavity 28 of cuff 16 using a known inflating tube 30 which runs along or may be embodied within the interior wall 32 of tracheal tube 12. The distal end 34 of tube 30 extends through the wall of tracheal tube 12 and forms a fluid tight attachment with inner wall 26 of cuff 16 so that inflating tube 30 may directly communicate with compartment 28 of cuff 16. It will be appreciated that a fluid type seal must be made between tube 30 and cuff 16 so that any fluid delivered through tube 30 flows directly into cavity 28 and is wholly contained within said cavity.

Neck portion 18 of cuff 16 is adhesively or otherwise (e.g. ultrasonically) bonded to the distal portion of tracheal tube 12 as shown in FIG. 2. In an important feature of the present invention, the distal end of tracheal tube 12 is positioned within cuff 16 such that distal end 36 will be completely enveloped by "cuff" 16 upon inflation thereof. In other words, inflatable "cuff" 16 is positioned on tracheal tube 12 so that the cuff will extend beyond the distal end of the tube to which it is attached and thereby protect end 36 and prevent end 36 from contacting the walls of the trachea 10.

The novel inflatable cuff means of the present invention overcomes the serious problems and complications of the prior art constant pressure inflatable cuffs.

In addition, the low pressure cuff means of the present invention compensates for variable airway pressure within the trachea. During use, tracheal tube 12 is positioned within the trachea in the known manner (such as is disclosed in my prior patents U.S. Pat. Nos. 4,471,776 and 4,340,046) and an appropriate compressible fluid is delivered via tube 30 into cavity 28 to thereby pressurize cuff 16 just enough to bring it gently against the mucosa of the tracheal wall. As airway pressure fluctuates with ventilatory requirements of the lungs, this pressure is transmitted to inflated cuff 16. Because cuff 16 has been inflated with a compressible fluid, the pressure on the cuff and consequently on the seal between the cuff and the tracheal wall also increases. Thus, the higher the pressure within the tracheobronchial system, the tighter the seal. Maximum pressure will occur at the end of the inspiratory phase of respiration. At the conclusion of expiration, the pressure against the mucosa reverts to 0 mm of mercury or the pressure necessary to bring it to the wall to form the initial seal. Thus, there is intermittent compression of the capillary blood flow only during the inspiratory phase of respiration avoiding tissue necrosis associated with tissue anoxia that accompanies the prolonged use of prior art cuffs requiring high Pressure necessary during some pathological states of the lungs or low flow states seen in shock.

Figure 5:
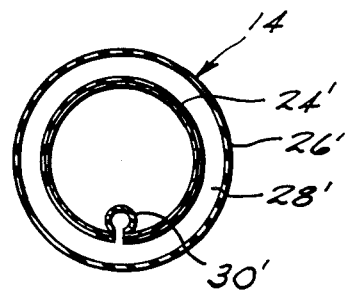
FIG. 5 is a cross sectional elevation view along the line 5—5 of FIG. 4.
Figure 4:
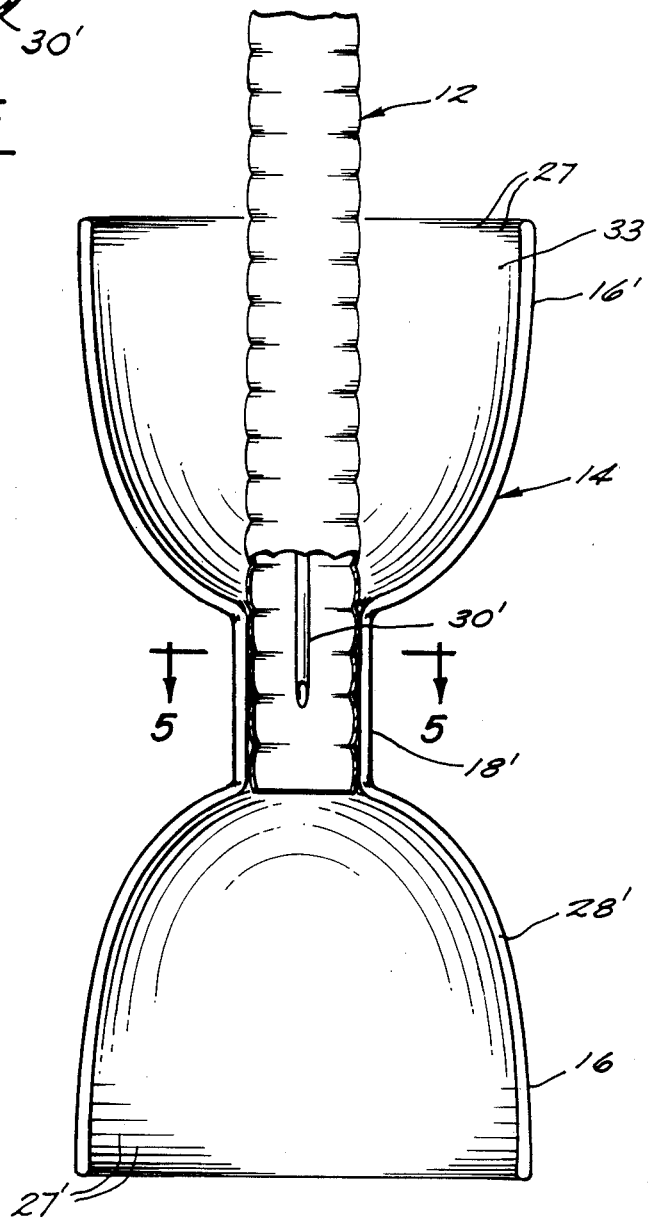
FIG. 4 is an enlarged view, partly in cross section of a second embodiment of a cuff in accordance with the present invention.

Turning now to FIGS. 1, 4 and 5, the preferred embodiment of the present invention is shown generally at 14. It will be appreciated that since cuff 16 of FIGS. 2 and 3 is specifically intended for respiratory control and is maintained expanded against the tracheal wall with minimal pressure, it is necessary to protect the pulmonary tree against aspiration of gastric contents, blood and other secretions. This is accomplished in a preferred embodiment of the present invention by placing a second funnel-like or paraboloid inflatable means 16' on the distal end of tube 12 with paraboloid section 16' being inverted with respect to paraboloid portion 16 so that the open end of paraboloid portion 16' is directed towards the larynx and may be expanded with minimal pressure against the tracheal wall as shown in FIG. 1. Accordingly, in the event that aspiration should occur, the fluids are effectively trapped in the opened reservoir 33 created around tube 12. Basically, cuff 14 has a similar construction to cuff 16 with the primary difference being the hourglass configuration thereof. Like cuff 16, the neck portion 18' will be adhesively or otherwise bonded along its inner surface to tracheostomy tube 12. Also like cuff 16, fluid inlet tube 30' will form a fluid tight communication with the hourglass shaped cavity 28' of cuff 14. Of course, while cuff 14 is depicted as a single inflatable compartment, it will be appreciated that inflatable paraboloid shaped cuff portions 16 and 16' may form two discrete inflatable members.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A tracheal tube for use in the trachea of respiratory patients comprising:
    tube means, said tube means terminating at a distal end, said tube means having an interior and an exterior;
    inflatable cuff means having the shape of a funnel-like paraboloid attached to said exterior of said tube means near said distal end, said cuff means enveloping and extending beyond said distal end when said cuff means is inflated, said cuff means having an inner wall and an outer wall defining therebetween an enclosed cavity for receiving a fluid, said cuff means being normally collapsed and being adapted for contacting the trachea and said cavity being pressurized to a pre-selected pressure level by delivery of a regulated amount of fluid therein so as to form and maintain a low pressure fluctuating seal with a wall of the trachea, said low pressure being defined as the minimal amount of pressure effective to exert said fluctuating seal against the wall of the trachea as airway pressure in the trachea fluctuates with the ventilatory requirements of the lungs wherein pressure exerted against a wall of the trachea by said seal is increased with increasing airway pressure and decreased with decreasing airway pressure and wherein said low pressure seal is exerted only during inspiration with substantially no pressure being exerted by said seal on a wall of the trachea at times other than inspiration.

2. The tube of claim 1 wherein: said cuff means includes a first end having a first diameter and a second end having a second diameter larger than said first diameter, said cuff means diverging outwardly between said first and second ends.

3. The tube of claim 2 wherein said cuff means further includes:
    a neck portion of substantially constant diameter, a central paraboloid portion and a terminal cylindrical skirt section, said neck portion defining said first end and said skirt section defining said second end.

4. The tube of claim 3 wherein: said neck portion is bonded to said tube means.

5. The tube of claim 2 wherein: said cuff means has a shape approximating an inverted paraboloid.

6. The tube of claim 2 wherein: said cavity comprises a plurality of interconnected annular passageways.

7. The tube of claim 1 including: fluid delivery means associated with said tube means for delivering fluid to said cavity, said fluid delivery means being in fluid tight communication with said cavity.

8. The tube of claim 1 wherein: said cuff means includes a first end having a first diameter and a second end having a second diameter, said cuff means further having a central Portion having a third diameter smaller than both said first and second diameters, said cuff means diverging outwardly from said central portion towards said first end, and said cuff means diverging outwardly from said central portion towards said second end.

9. The tube of claim 8 wherein: said central portion has a substantially constant diameter.

10. The tube of claim 8 wherein: said cuff means has a shape approximating an hour glass.

11. The tube of claim 8 wherein: said cuff means has a shape approximating a pair of inverted paraboloids.

12. The tube of claim 1 wherein: said cuff is comprised of polyvinyl chloride or polyurethane.

13. THe tube of claim 1 wherein: said cavity has a pressure of less than or equal to about 10 mm of mercury.

14. A trachea tube for use in the trachea of respiratory patients comprising:
    tube means, said tube means terminating at a distal end, said tube means having an interior and an exterior;
    first inflatable cuff means attached to said exterior of said tube means near said distal end, said first cuff means being positioned on said tube means so that said cuff means envelopes and extends beyond said distal end when said cuff means is inflated; and
    second inflatable cuff means attached to said exterior of said tube means and spaced upwardly from said first cuff means, said second cuff means including reservoir means;
    said first and second cuff means having the shape of a funnel-like paraboloid each having an inner wall and an outer wall defining therebetween an enclosed cavity for receiving a fluid, said first and second cuff means being normally collapsed and being adapted for contacting the trachea and said cavity being pressurized to a pre-selected pressure level by regulating the amount of fluid delivered therein so as to form and maintain a low pressure fluctuating seal with a wall of the trachea, said low pressure being defined as the minimal amount of pressure effective to exert said fluctuating seal against the wall of the trachea as airway pressure in the trachea fluctuates with the ventilatory requirements of the lungs wherein pressure exerted against a wall of the trachea by said seal is increased with increasing airway pressure and decreased with decreasing airway pressure and wherein said low pressure seal is exerted only during inspiration with substantially no pressure being exerted by said seal on a wall of the trachea at times other than inspiration.

15. The tube of claim 14 wherein:
said first and second cuff means each includes a first end having a first diameter and a second end having a second diameter larger than said first diameter, said cuff means diverging outwardly between said first and second ends.

16. The tube of claim 15 wherein said first and second cuff means each further includes:
a neck portion of substantially constant diameter, a central paraboloid portion and a terminal cylindrical skirt section, said neck portion defining said first end and said skirt section defining said second end.

17. The tube of claim 16 wherein:
said neck portion is bonded to said tube means.

18. The tube of claim 14 wherein:
said first and second cuff means each has a shape approximating a paraboloid.

19. The tube of claim 19 including:
fluid delivery means associated with said tube means for delivering fluid to said cavity, said fluid delivery means being in fluid tight communication with said cavity.

20. The tube of claim 14 wherein:
said first and second cuff means have an overall shape approximating an hour glass.

21. The tube of claim 14 wherein:
said first and second cuff means have a shape approximating a pair of inverted paraboloids.

22. The tube of claim 14 wherein:
said cavity comprises a plurality of interconnected annular passageways.

23. The tube of claim 14 wherein:
said cuff is comprised of polyvinyl chloride or polyurethane.

24. The tube of claim 14 wherein:
said cavity has a pressure of less than or equal to about 10 mm of mercury.

25. A tracheal tube for use in the trachea of respiratory patients comprising:
tube means, said tube means terminating at a distal end, said tube means having an interior and an exterior;
inflatable cuff means attached to said exterior of said tube means near said distal end, said cuff means being positioned on said tube means so that said cuff means envelopes and extends beyond said distal end when said cuff means is inflated, said cuff means including a first end having a first diameter and a second end having a second diameter larger than said first diameter, said cuff means diverging outwardly between said first and second ends, said cuff means also having an inner wall and an outer wall defining therebetween a cavity, said cavity comprising a plurality of interconnected annular passageways.

26. A tracheal tube for use in the trachea of respiratory patients comprising:
tube means, said tube means terminating at a distal end, said tube means having an interior and an exterior;
first inflatable cuff means attached to said exterior of said tube means near said distal end, said first cuff means being positioned on said tube means so that said cuff means envelopes and extends beyond said distal end when said cuff means is inflated;
second inflatable cuff means attached to said exterior of said tube means and spaced upwardly from said first cuff means, said second cuff means including reservoir means; and
wherein said first and second cuff means each includes a first end having a first diameter and a second end having a second diameter larger than said first diameter, said cuff means diverging outwardly between said first and second ends, said cuff means also having an inner wall and an outer wall defining therebetween a cavity, said cavity comprising a plurality of interconnected annular passageways.

27. A tracheal tube for use in the trachea of respiratory patients comprising:
tube means, said tube means terminating at a distal end, said tube means having an interior and an exterior;
inflatable means attached to said tube means, said inflatable means being in contact with the trachea and forming a fluctuating seal with a wall of the trachea, said inflatable means exerting said fluctuating seal against the wall of the trachea as airway pressure in the trachea fluctuates with the ventilatory requirements of the lungs wherein said seal is increased with increasing airway pressure and decreased with decreasing airway pressure; and
said inflatable means including a first end having a first diameter and a second end having a second diameter larger than said first diameter, said cuff means diverging outwardly between said first and second ends, said cuff means having an inner wall and an outer wall defining therebetween a cavity, said cavity comprising a plurality of interconnected annular passageways.

* * * * *